United States Patent [19]
Redmond

[11] Patent Number: 5,677,763
[45] Date of Patent: Oct. 14, 1997

[54] OPTICAL DEVICE FOR MEASURING PHYSICAL AND OPTICAL CHARACTERISTICS OF AN OBJECT

[75] Inventor: Robert Redmond, Toledo, Ohio

[73] Assignee: Technology Resources, Inc., Toledo, Ohio

[21] Appl. No.: 689,366

[22] Filed: Aug. 8, 1996

[51] Int. Cl.[6] .......................... G01N 21/00; G01B 11/24
[52] U.S. Cl. ................................................ 356/73; 356/376
[58] Field of Search ........................... 356/71–73, 394, 356/378, 375–376, 384, 387, 390; 382/41, 46, 30; 250/566–568, 234–236, 578, 203 R, 231, 613, 570; 244/3.13, 3.16

[56] References Cited

U.S. PATENT DOCUMENTS

| | | | |
|---|---|---|---|
| 3,647,961 | 3/1972 | Blitchington, Jr. et al. | 178/7.85 |
| 3,708,680 | 1/1973 | Calhoun | 250/223 |
| 4,024,573 | 5/1977 | Carnes | 358/87 |
| 4,258,976 | 3/1981 | Scott et al. | 350/96.2 |
| 4,376,582 | 3/1983 | Kirchner et al. | 356/71 |
| 4,465,374 | 8/1984 | Pryor et al. | 356/375 |
| 4,620,235 | 10/1986 | Watt | 358/293 |
| 4,637,718 | 1/1987 | Kirchner et al. | 356/71 |
| 4,710,004 | 12/1987 | Verhaagen | 353/81 |
| 4,717,823 | 1/1988 | Steimel et al. | 250/236 |
| 4,737,614 | 4/1988 | Richardson | 219/130 |
| 4,906,099 | 3/1990 | Casasent | 356/394 |
| 4,960,313 | 10/1990 | Yamanaka | 350/6.1 |
| 5,196,683 | 3/1993 | Maron et al. | 235/462 |
| 5,225,924 | 7/1993 | Ogawa et al. | 359/196 |
| 5,365,288 | 11/1994 | Dewald et al. | 353/98 |

*Primary Examiner*—Frank G. Font
*Assistant Examiner*—Michael P. Stafira
*Attorney, Agent, or Firm*—Brinks Hofer Gilson & Lione

[57] ABSTRACT

An optical device for measuring and inspecting a physical and optical characteristic of an object. In the preferred embodiment, the optical device comprises a light source emitting a beam of light rays along an optical axis, a light-sensitive electronic device, preferably a charge-coupled device, positioned along the optical axis converting an image formed from the beam of light rays being reflected from the object into an electrical signal. An image rotating device, preferably a Dove prism, is positioned along the optical axis between the object and the light-sensitive electronic device. A rotating device rotates the image rotating device at an angle of rotation. The rotating device, preferably a d-c step motor, converts the angle of rotation of the image rotating device into an electrical signal. The angle of rotation of the image rotating device is based on a step position of the d-c step motor. The optical device determines physical and optical characteristics of the object based on the strength of the electrical signal from the light-sensitive electronic device and the electrical signal from the d-c step motor.

22 Claims, 4 Drawing Sheets

OPTICAL DEVICE FOR MEASURING PHYSICAL AND OPTICAL CHARACTERISTICS OF AN OBJECT

BACKGROUND OF THE INVENTION

1. Field of the Invention

The invention relates to optical measuring and inspecting devices, and in particular, to an optical device for measuring physical and optical characteristics of an object by using a rotating Dove prism in combination with a one-dimensional charge coupled device.

2. Related Art

In conventional imaging devices, photosensitive elements or sites are usually arranged in a two-dimensional array. For example, a typical two-dimensional array may contain 380 scan lines and 488 photosensitive elements for each scan line, or a total of 185,440 photosensitive elements. In RS-170 devices, such as cathode ray tube devices and camcorder devices, the image is scanned at a rate of thirty (30) frames/second. Thus, a large amount of information (over 5.5 million pixels/second) needs to be obtained and manipulated in order to accurately measure and inspect a stationary object.

In the medical imaging field, for example, increased resolution has produced two-dimensional arrays containing 1024 scan lines and 1024 photosensitive elements for each scan line. Consequently, the amount of information needed to be manipulated in order to measure and inspect an object is greatly increased. As a result, the scan rate is usually decreased to be less than thirty (30) frames/sec in order to manipulate the large amount of information. In addition, the increased resolution and large two-dimensional arrays are much more costly than the lower resolution devices.

To overcome the problems associated with large two-dimensional arrays of photosensitive elements while achieving high resolution, one line of photosensitive elements (photo sites) or line arrays are used to sense a moving object as it travels past the one-dimensional line sensor array. Usually the object travels past the one-dimensional line sensor so that the data can be properly manipulated by the processor. One advantage of the one-dimensional line array is that each photosensitive element can be automatically compensated for each photosensitive element history due to the smaller number of photosensitive elements as compared to two-dimensional arrays. Another advantage is that data from each photosensitive element can be easily manipulated by the processor. As a result, the integrity of the data is much better as compared to two-dimensional arrays. However, the object must be scanned by the one-dimensional line sensor array in order for the data to be properly manipulated by the processor.

One solution was to rotate a Dove prism or Pechan prism while moving a single photosensitive element to create a spiral pattern of the stationary object. However, the amount of information obtained was based on the movement speed of the photosensitive element and the rotation speed of the Dove prism. Thus, there is a need to produce a fast high resolution image for inspecting and measuring an object while rotating the Dove prism and without moving the photosensitive elements by using a one-dimensional line sensor array.

SUMMARY OF THE INVENTION

In view of the foregoing, it is an object of the invention to provide an optical device for measuring and inspecting physical and optical characteristics of an object while having the advantages of a line array device to produce high resolution images without moving the object past the one-dimensional line sensor array. The optical device comprises a light source that emits a beam of light, a light-directing device that directs the beam of light towards the object along an optical axis, a light-sensitive electronic device positioned in the optical axis for converting an image formed from the beam of light, an image rotating device, preferably a Dove prism or Pechan prism, positioned between the object and the light-sensitive device in the optical axis, an aperture stop positioned between the object and the image rotating device, a rotating device for rotating the image rotating device, and a processor for processing the electrical signal from the light-sensitive electronic device. The optical device provides an image resolution of approximately one micron or less.

These and other aspects and advantages of the invention are described or apparent from the following detailed description of the preferred embodiments and appended drawings wherein like reference numbers refer to the same element, feature or component.

BRIEF DESCRIPTION OF THE DRAWINGS

The preferred embodiments are described with reference to the drawings in which.

DETAILED DESCRIPTION OF THE PREFERRED EMBODIMENTS

Figure 1:
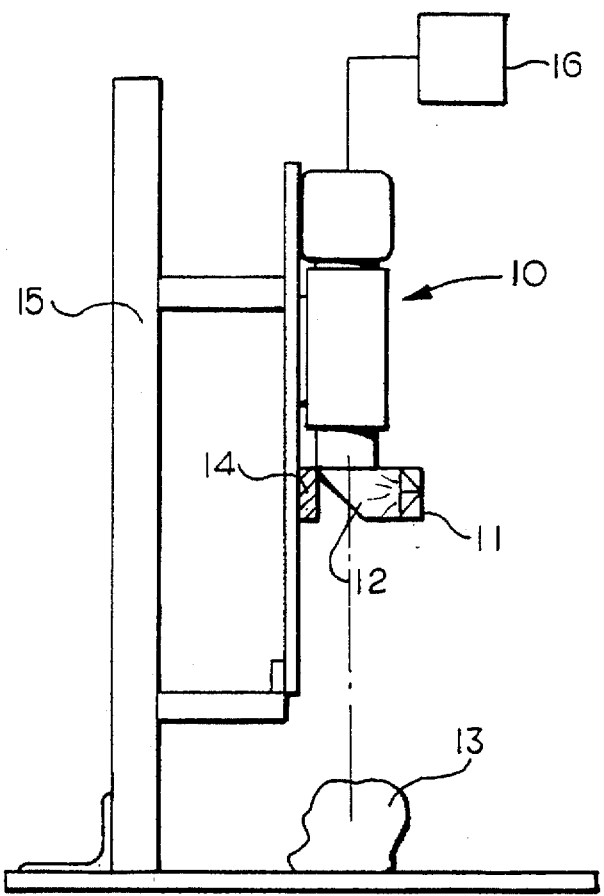
FIG. 1 shows a side view of the optical device for measuring and inspecting physical characteristics of an object according to a preferred embodiment of the invention.

FIG. 1 shows a side view of the optical device for measuring and inspecting physical characteristics of an object according to a preferred embodiment of the invention.

In the preferred embodiment of the invention, the optical device 10 is mounted on a frame structure 15. Frame structure 15 maintains the optical device 10 at a distance from an object 13 to be measured and inspected. The optical device 10 includes a light source 11 for emitting a beam of light rays and by a beam splitter 12 for splitting the beam of light rays emitted by light source 11. The light rays reflected by beam splitter 12 are directed towards object 13 along an optical axis (dotted lines) of the optical device 10. The light rays passing through beam splitter 12 may be absorbed by a well-known light absorbing material 14 to prevent backscatter of the light beam.

It should be appreciated by those skilled in the art that optical device be can be practiced with or without beam splitter 12 by using other well-known light sources. For example, by using a fluorescent light ring positioned around object 13, optical device 10 may not require beam splitter 12.

Figure 2:
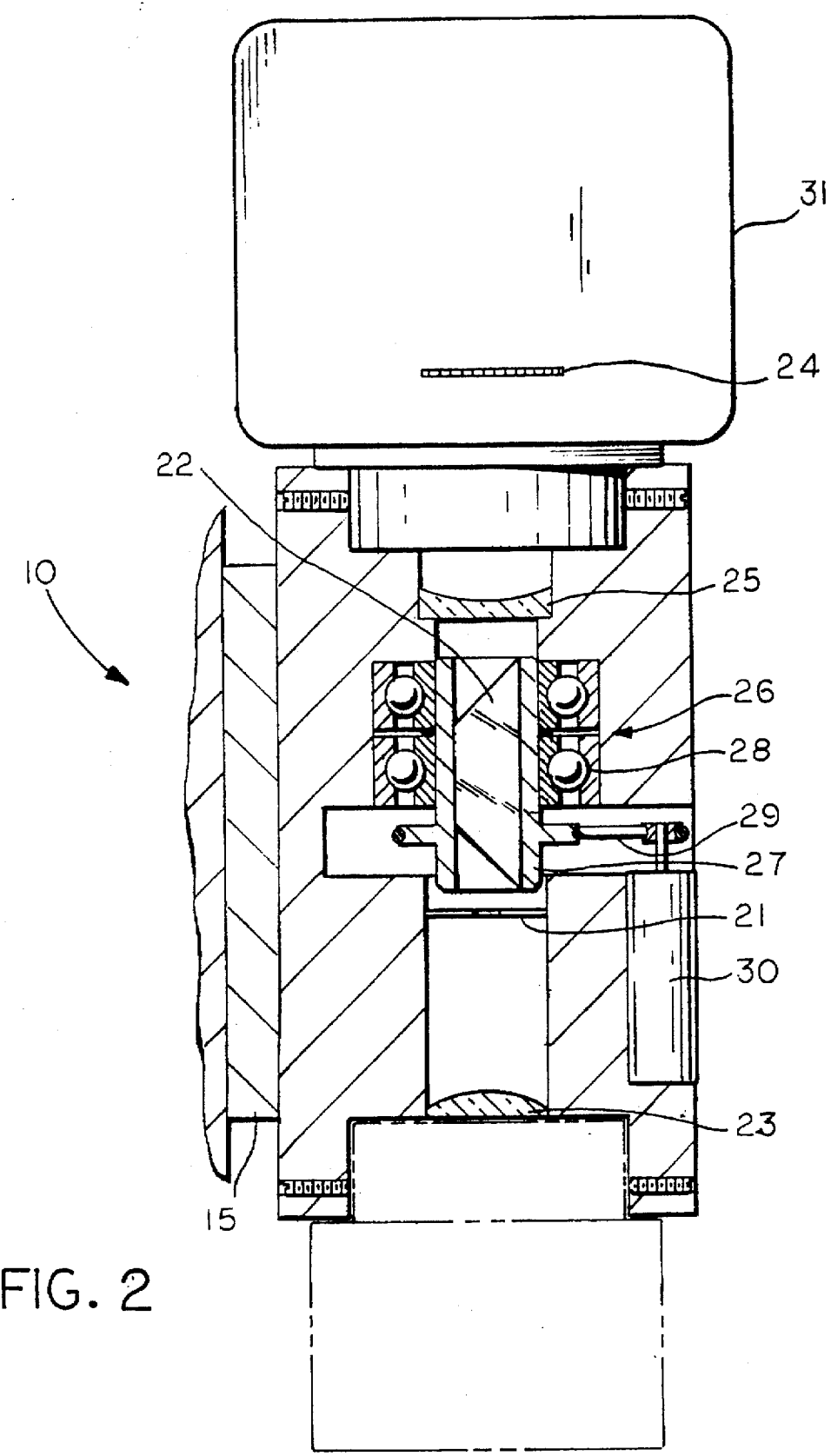
FIG. 2 shows a side perspective view of the optical device according to the preferred embodiment of the invention.

FIG. 2 shows a side perspective view of the optical device 10 according to the preferred embodiment of the invention. The light rays that are reflected by object 13 travel back towards beam splitter 12 along the optical axis of optical device 10. The reflected light rays pass through beam splitter 12 and travel through an aperture stop 21 and towards an image rotating device 22. In the preferred embodiment, image rotating device 22 comprises a Dove prism. However, it should be appreciated by those skilled in the art that image rotating device 22 may also comprise a Pechan prism, a mirror arrangement or other optical devices capable of rotating the image of object 13. A lens 23, preferably a plano-convex lens, may be positioned between object 13 and aperture stop 21 for magnifying object 13.

In the preferred embodiment, image rotating device 22 is disposed between beam splitter 12 and a light-sensitive electronic device 24, preferably a charged coupled device (CCD), that senses the light rays passing through the image rotating device 22. The light-sensitive electronic device 24 converts the sensed light rays into an electrical signal for processing by a well-known processor or computer means 16 (FIG. 1). It should be appreciated by those skilled in the art that processor means 16 may comprise any processing means, such as a personal computer, a laptop computer, or any other data processing device. The light-sensitive electronic device 24 may be disposed within a well-known camera body 31. Another lens 25, preferably a plano-concave lens, for magnifying the object may be positioned between the image rotating device 22 and the light-sensitive electronic device 24.

In the preferred embodiment, the light-sensitive electronic device 24 comprises a charge-coupled device (CCD) having a one-dimensional linear array of 2048 photosensitive detector elements. However, it should be appreciated by one skilled in the art that the invention is not limited by 2048 photosensitive detector elements and that the invention can be practiced with a CCD having any number of photosensitive detector elements.

Image rotating device 22 may be fixedly attached within a tube assembly 26 by any means well known to those skilled in the art, such as by friction mounting or glueing. Tube assembly 26 comprises a tube 27 rotatably mounted using ball bearings 28. Tube assembly 26 and image rotating device 22 mounted therein may be rotated by a pulley belt 29 connected to an image rotating means or device 30. In the preferred embodiment, image rotating means 30 comprises a d-c step motor. However, it should be appreciated that the image rotating means 30 of the invention is not limited to a d-c step motor and that the invention can be practiced using other image rotating means 30, such as an a-c motor and other well-known devices for driving pulley belt 29 in a rotating manner.

Figure 3:
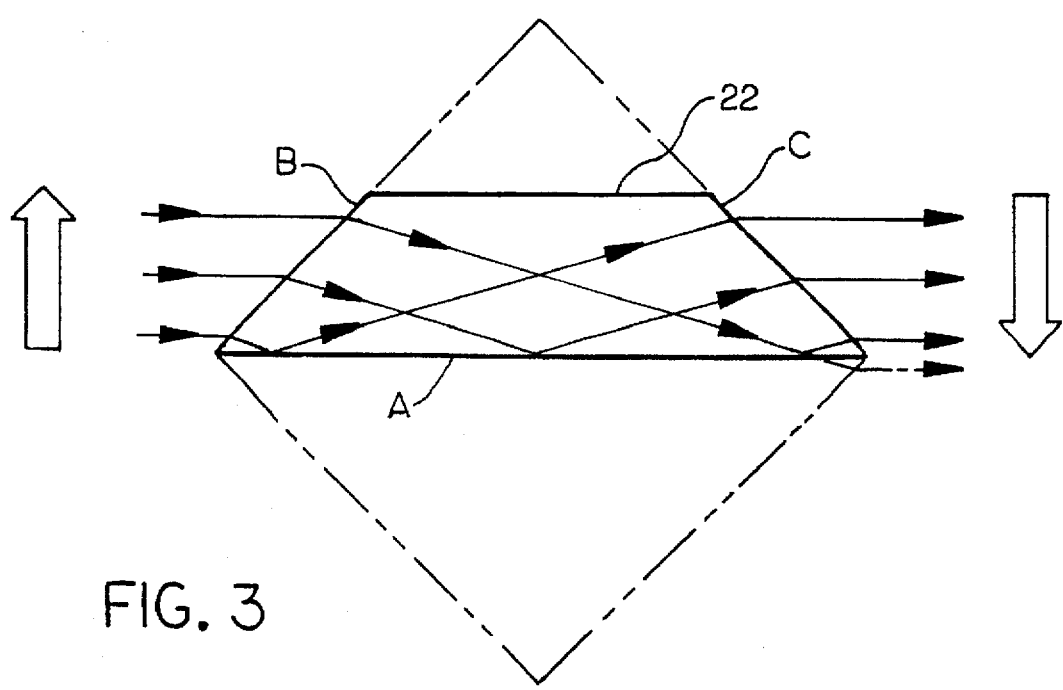
FIG. 3 shows ray tracing of a beam of light as it passes through the Dove prism according to the preferred embodiment of the invention.

In the preferred embodiment, the step positions of d-c step motor 30 increment from 0 to 2047 (i.e., a total of 2048 step positions) to correspond to one full revolution (i.e., 360° rotation) of the image rotating device. In other words, when d-c motor 30 is incremented from a start step position of 0 to an end step position of 2047, processor 16 determines that image rotating device 22 has rotated one full revolution. However, it should be appreciated that the invention is not limited to a particular number of step positions and that any number of step positions may be used. In this manner, processor 16 provides a means for processing information received from the light-sensitive electronic device 24 or CCD line array and d-c step motor 30. Specifically, processor 16 processes an electrical signal representing light intensities sensed by each 2048 photosensitive detector elements of light-sensitive electronic device 24 or CCD line array and determines a rotation angle of the image rotating device 22 based on the step position of d-c step motor Referring now to FIG. 3, the image rotating device 22 is shown in the preferred embodiment as a Dove prism 22. The Dove prism 22 permits on-axis inversion of the image with a single reflecting surface. The light rays from object 13 arrive parallel to the hypotenuse face A of Dove prism 22. After being refracted downward at the entrance face B, the light rays are reflected upward from the hypotenuse face A and emerge after a second refraction at the exit face C. Since the apex of Dove prism 22 is not used by the light beam, the apex of Dove prism 22 may be truncated. As seen in FIG. 3, Dove prism 22 performs an on-axis inversion of the image of the arrow by using a single reflecting surface or hypotenuse face A.

An important feature of the invention is that the rotation of Dove prism 22 by d-c step motor 29, in combination with light-sensitive electronic device 24, rapidly and accurately measures and inspects physical and optical characteristics of object 13. This is accomplished by positioning object 13 to be measured and inspected on the optical axis of optical device 10. Light rays emitted from light source 11 are reflected from object 13 and pass through beam splitter 12, through aperture 21 and rotating Dove prism 22 and strike light-sensitive electronic device 24. Although object 13 remains stationary, the beam of light rays from the image of object 13 are rotated by the rotating Dove prism 22 and are sensed by light-sensitive electronic device 24 to produce an electrical signal based on the intensity of the beam of light rays.

At the same time, d-c step motor 30 converts a position of the rotating Dove prism 22 into an electrical signal based on the step position of d-c step motor 30. Electrical signals generated by light-sensitive electronic device 24 and d-c step motor 30 are processed by processor 30 to determine a physical and an optical characteristic of object 13.

Figure 9:
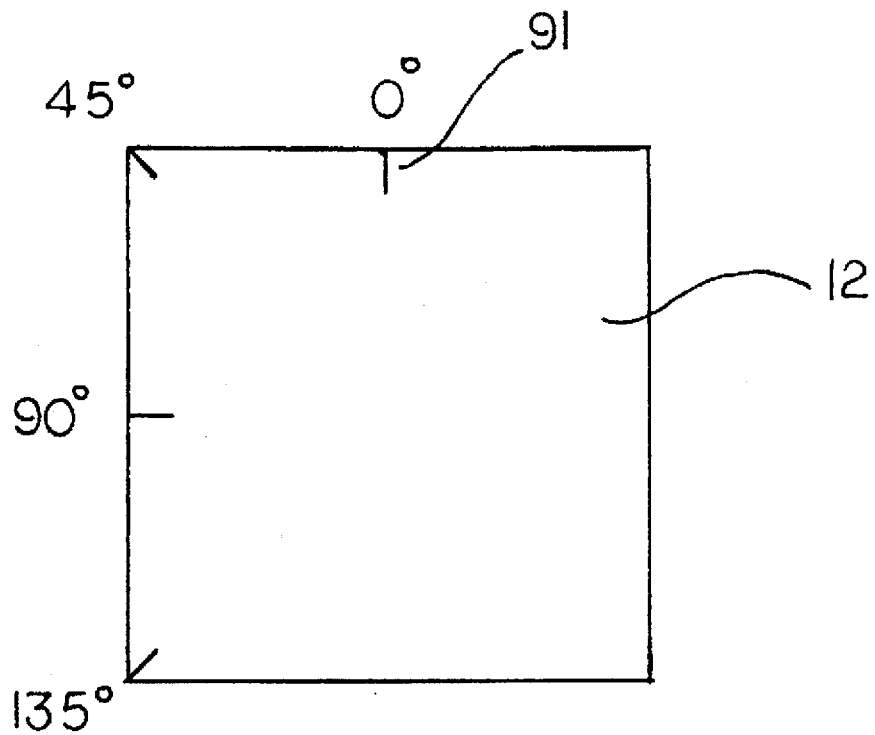
FIG. 9 shows a beam splitter having opaque markings in accordance with an alternative embodiment of the invention.

FIG. 9 show an alternative embodiment of the invention in which the d-c step motor 30 can be replaced by inscribing opaque markings 91 on beam splitter 12. The opaque markings 91 can be positioned on beam splitter 12 at angles of 0°, 45°, 90° and 135°. Rotation of the image of object 13 by the rotating Dove prism 22 causes light-sensitive electronic device 24 to send an electronic signal to processor 16 indicating the presence of the opaque markings 91 at these angles. It should be understood that opaque markings at these angles provide enough information to processor 16 to determine the angle of rotation of Dove prism 22 for one complete revolution. In this manner, the opaque markings 91 of beam splitter 12 can indicate a position of the rotating Dove prism.

One physical characteristic that can be determined by optical device 10 is a shape of object 13. This is accomplished by comparing the light intensity received from object 13 with the light intensity received from the background area surrounding object 13. In this manner, optical device 10 determines the location of the edges of object 13. Using the location of the edges of object 13, as well as, the step position of d-c step motor 29 to determine the rotation angle of Dove prism 22, optical device 10 can determine the shape of object 13. For example, optical device 10 can measure and inspect the roundness or squareness of object 13 as described below.

Figure 4:
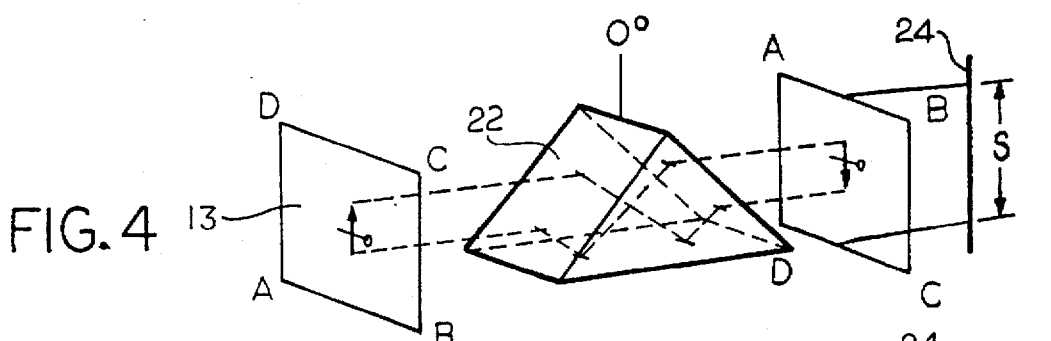
FIG. 4 shows the orientation of the image of the object as the Dove prism is rotated at an angle of FIG. 5 shows the orientation of the image of the object as the Dove prism is rotated at an angle of 22.5°.

FIG. 4 shows the orientation of the image of object 13 when the hypotenuse face A of Dove prism 22 is at an angle of 0° with respect to object 13. In FIG. 4, the arrow and cross bar pattern (line with circle) is shown to be inverted from top to bottom, but not left to right.

In FIG. 4, object 13 is initially oriented such that two opposing parallel sides, AB and CD, of object 13 are parallel to the hypotenuse face A of Dove prism 22 and the other two opposing parallel sides, AD and BC, of object 13 are perpendicular to the hypotenuse face A of Dove prism 22. At this time, processor 16 determines that Dove prism 22 is at a rotation angle of 0° based on electrical signals from d-c step motor 30, indicating that the step position of d-c step motor 30 is at the start step position of zero (0). At this position, processor 16 may determine, based on electrical signals from the light-sensitive electronic device 24, that object 13 is located between photosensitive elements 500.000 and 1500.000 of light-sensitive electronic device 24. This is accomplished by comparing the electrical signal strength from object 13 to the electrical signal strength from the background area surrounding object 13. For example, the light-sensitive electronic device 24 may transmit a stronger electrical signal to processor 16 to indicate object 13 and a weaker electrical signal to processor 16 to indicate the background area surrounding object 13. In this manner, processor 16 can determine, based on the electrical signals strengths from the light-sensitive electronic device 24 and the electrical signal from d-c step motor 30, that object 13 has a dimension, S, across opposing parallel sides AB and CD of approximately 1000.000 (i.e., 1500.000–500.000) photosensitive elements when Dove prism 22 is at an angle of 0°.

Figure 5:
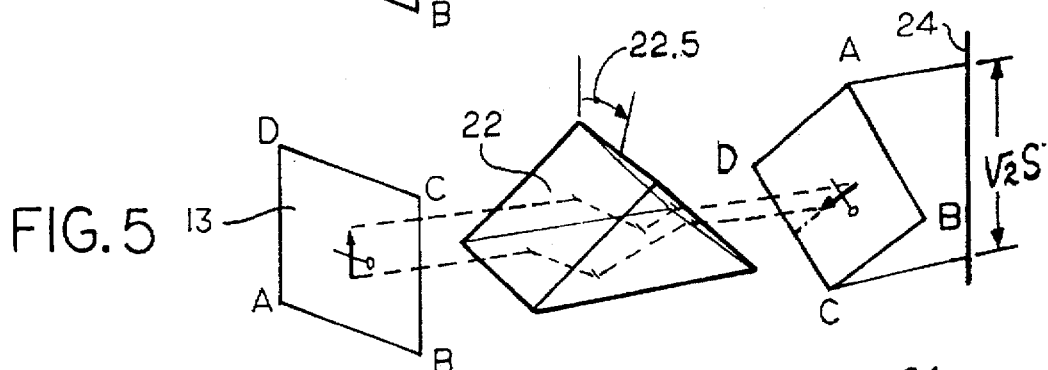

In FIG. 5, the hypotenuse face A of Dove prism 22 has been rotated to an angle of 22.5° with respect to object 13. In other words, the hypotenuse face A of Dove prism 22 has been rotated 22.5° relative to the angle (0°) of the hypotenuse face A of Dove prism 22 shown in FIG. 4. As seen in FIG. 5, Dove prism 22 causes the beam of light rays forming the image of object 13 to rotate to an angle of 45° relative to the light rays forming the image of object 13 shown in FIG. 4. In other words, Dove prism 22 has been rotated to ⅛ of a full revolution (22.5°) and d-c step motor 29 is at a step position of approximately 256 (i.e., 2048/8). Thus, the image of object 13 is rotated twice as fast as the hypotenuse face A of Dove prism 22. In this position, processor 16 determines, based on the electrical signal strengths from light-sensitive electronic device 24 and from the electrical signal from d-c step motor 30, that object 13 is located between photosensitive elements 292.893 and 1707.107 when Dove prism has been rotated at an angle of 22.5°. As a result, the processor 16 determines that the object has a dimension, √2 S, across the diagonal AC of approximately 1414.214 (i.e., √2×1000.000) photosensitive elements.

Figure 6:
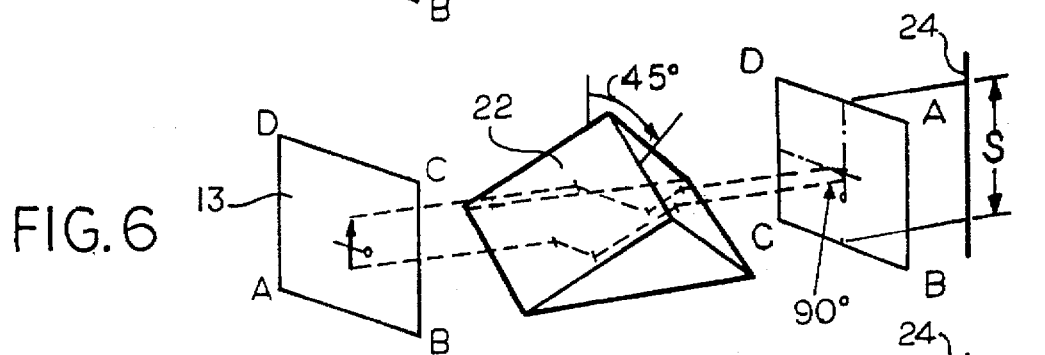
FIG. 6 shows the orientation of the image of the object as the Dove prism is rotated at an angle of 45°.

In FIG. 6, the hypotenuse face A of Dove prism 22 has been rotated to an angle of 45° relative to the angle (0°) of Dove prism 22 shown in FIG. 4. As seen in FIG. 6, Dove prism 22 causes the beam of light rays forming the image of object 13 to be rotated to an angle of 90° relative to the angle (0°) of the image of object 13 shown in FIG. 4. In other words, Dove prism 22 has been rotated to ¼ of a full revolution and d-c step motor 30 is located at a step position of approximately 512 (2048/4). In this position, processor 16 determines, based on the electrical signal strengths from the light-sensitive electronic device 24 and from the electrical signal from d-c step motor 30, that object 13 is between photosensitive elements 500.000 and 1500.000 when Dove prism has been rotated at an angle of 45°. As a result, processor 16 determines that object 13 has a dimension, S, across the opposing sides AD and BC of approximately 1000.000 photosensitive elements.

Figure 7:
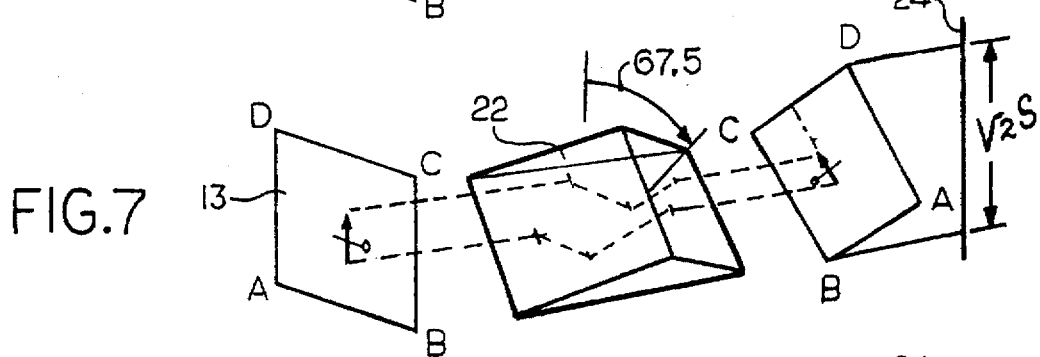
FIG. 7 shows the orientation of the image of the object as the Dove prism is rotated at an angle of 67.50°.

In FIG. 7, the hypotenuse face A of Dove prism 22 has been rotated to an angle of 67.5° relative to the angle (0°) of Dove prism 22 shown in FIG. 4. As seen in FIG. 7, Dove prism 22 causes the beam of light rays forming an image of object 13 to be rotated to an angle of 135° relative to the angle (0°) of the image of object 13 shown in FIG. 4. In other words, Dove prism 22 has been rotated to ⅜ of a full revolution and d-c step motor 30 is at a step position of approximately 768 (2048/3/8). In this position, processor 16 determines, based on the electrical signal strengths from the light-sensitive electronic device 24 and from the electrical signal from d-c step motor 30, that object 13 is between photosensitive elements 292.893 and 1707.107 when Dove prism has been rotated at an angle of 67.5°. As a result, the processor 16 determines that object 13 has a dimension, √2 S, across the diagonal BD of approximately 1414.214 (i.e., √2×1000.000) photosensitive elements.

Figure 8:
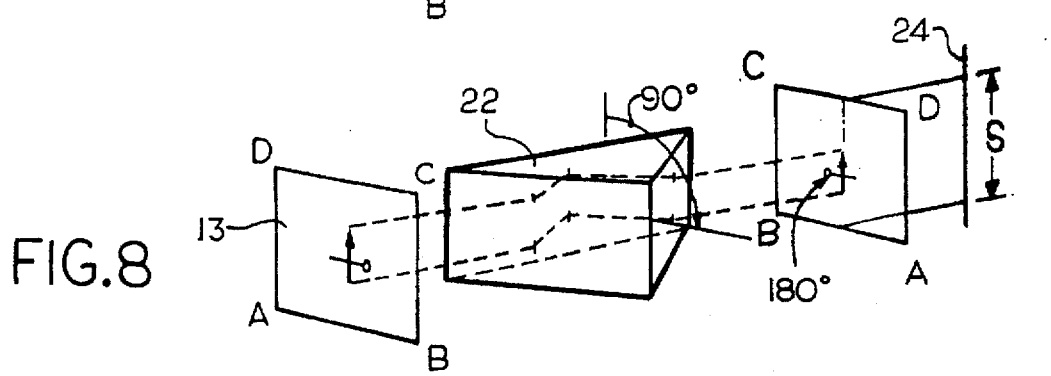
FIG. 8 shows the orientation of the image of the object as the Dove prism is rotated at an angle of 90°.

In FIG. 8, the hypotenuse face A of Dove prism 22 has been rotated to an angle of 90° relative to the angle (0°) of Dove prism 22 shown in FIG. 4. As seen in FIG. 8, the rotation of Dove prism 22 causes the beam of light rays forming the image of object 13 to rotate to an angle of 180° relative to the angle (0°) of the image of object 13 shown in FIG. 4. At this time, d-c step motor 30 is located at step position 1024 (2048/2). In this position, processor 16 determines, based on the electrical signal strengths from the light-sensitive electronic device 24 and the electrical signal from d-c step motor 30, that object 13 is between photosensitive elements 500.000 and 1500.000 when Dove prism has been rotated 90°. As a result, processor 16 determines that object 13 has a dimension across the opposing sides AB and CD of approximately 1000.000 photosensitive elements.

Likewise, the processor 16 will determine the dimension of the object 13 based on the electrical signal strengths from light-sensitive electronic device 24 for all other step positions (0–1024) of d-c step motor 30 and all other corresponding Dove prism rotation angles (0°–90°) not mentioned above. For simplicity, the dimensions determined by processor 16 for the other step positions and Dove prism rotation angles are omitted. However, it should be appreciated that processor 16 can determine that the dimension of object 13 will be between 1000.000 and 1414.214 photosensitive elements for these step positions and rotation angles based on the electrical signal strengths from light-sensitive electronic device 24 and the electrical signal from d-c step motor 30.

At this point, the optical device 10 can determine whether the shape of the object 13 is substantially square. This is accomplished by the processor 16 comparing the dimensions of the object 13 when the hypotenuse face A of the Dove prism 22 is located at rotation angles of 0°, 45° and 90° and corresponding step positions of 0, 512 and 1024, i.e., when the opposing sides AB, BC, CD and AD of the object 13 are perpendicular to the CCD line array 24. If the object 13 is substantially square, then the dimension of the object 13 will be approximately 1000.000 photosensitive elements at these rotation angles. On the other hand, if the object 13 is not substantially square, then the dimension of the object 13 will not be approximately equal to each other at these rotation angles and corresponding step positions.

Similarly, processor 16 can compare the dimension of object 13 when the hypotenuse face A of Dove prism 22 is located at rotation angles of 22.5° and 67.5° and corresponding step positions of 256 and 768, i.e., when the diagonals AC and BD are perpendicular to the light-sensitive electronic device 24. If object 13 is substantially square, then object 13 will have a dimension of approximately 1414.214 photosensitive elements at these rotation angles. Likewise, processor 16 can compare other Dove prism rotation angles between 0° and 90° based on the step position of the d-c step motor 30 and the electrical signal strengths of the CCD line array 24 to determine whether object 13 is substantially square at these other rotation angles. It should be apparent that rotating Dove prism 22 at rotation angles of greater than 90° will provide redundant information that is not needed to determine the entire shape of object 13. Thus, by rotating Dove prism 22 by a relative rotation angle of 90°, optical device 10 can rapidly measure and inspect the physical characteristics of object 13.

From the above example, it should be appreciated that optical device 10 can accurately and rapidly measure and inspect a physical characteristic of a dimension or shape of object 13 by rotating the Dove prism 22 by one-quarter of a full rotation (0°–90°) and by sensing the light intensity of the beam of light reflected by object 13. It should also be appreciated by those skilled in the art that optical device 10 is not limited to measuring or inspecting whether an object is substantially square and that the invention can be practiced to determine any shape of an object.

In the previous example, optical device 100 determines the physical characteristic of object 13 such as shape, by comparing the light intensities from object 13 converted into electrical signals with the light intensities converted into electrical signals from the background area surrounding object 13. In this manner, the difference in the electrical signal strengths define the edge location of object 13. The edge location of object 13 is determined by processor 16 for all Dove prism rotation angles to determine whether the object shape, for example, is substantially square.

In addition to measuring physical characteristics of object 13, optical device 10 can measure optical characteristics, such as process variances or defects, of object 13. This is accomplished by processor determining the uniformity or variations of light intensity over a surface area of the object 13 while the Dove prism 22 is being rotated. For example, light-sensitive electronic device 24 may transmit a strong electrical signal to processor 16 to indicate a white area within object 13 and a weak electrical signal to processor 16 to indicate a black area within object 13 while an image of object 13 is being rotated by Dove prism 22. In this manner, processor 16 can determine the total amount of dark areas on a white piece of paper, for example, or the number of inclusions or flaws in a diamond. It should be appreciated by one skilled in the art that the invention is not limited by the above examples and that the invention can be practiced to determine other physical and optical characteristics of the object.

While this invention has been described in conjunction with specific embodiments, it is evident that many alternatives, modifications and variations will be apparent to those skilled in the art. Accordingly, the preferred embodiments of the invention as set forth herein are intended to be illustrative, rather than limiting various changes may be made without departing from the spirit and scope of the invention as defined in the following claims.

What is claimed is:

1. An optical device for determining physical and optical characteristics of an object, comprising:
    a light source for emitting a beam of light rays;
    a beam splitter having opaque markings, said beam splitter directing the beam of light rays towards the object along an optical axis;
    a one-dimensional light-sensitive electronic device positioned along the optical axis, said light-sensitive electronic device converting a two-dimensional image formed from the beam of light rays being reflected from the object and the image formed from the opaque markings on said beam splitter into an electrical signal;
    an image rotating device positioned along the optical axis between said beam splitter and said light-sensitive electronic device for rotating an image of the object; and
    a rotating device for rotating said image rotating device at an angle of rotation with respect to the optical axis,
    wherein said optical device determines physical and optical characteristics of the object based on the electrical signal from said light-sensitive electronic device.

2. An optical device according to claim 1, further comprising an aperture stop positioned between the object and said image rotating device.

3. An optical device according to claim 2 further comprising a lens positioned between the object and said aperture stop.

4. An optical device according to claim 3, wherein said lens comprises a plano-convex lens.

5. An optical device according to claim 1, wherein said image rotating device comprises a Dove prism.

6. An optical device according to claim 1, wherein said rotating device comprises a dc step motor.

7. An optical device according to claim 1, wherein said light-sensitive electronic device comprises a charge-coupled device.

8. An optical device according to claim 7, wherein said charge-coupled device comprises 2048 photosensitive elements.

9. An optical device according to claim 1, further comprising a lens positioned between said image rotating device and said light-sensitive electronic device.

10. An optical device according to claim 9, wherein said lens comprises a plano-concave lens.

11. An optical device for determining a physical characteristic of an object, comprising:
    a light source for emitting a beam of light rays along an optical axis;
    a beam splitter having opaque markings, said beam splitter directing the beam of light rays towards the object along the optical axis;
    a one-dimensional light-sensitive electronic device positioned along the optical axis, said light-sensitive electronic device converting a two-dimensional image formed from the beam of light rays being reflected from the object and the image formed from the opaque markings on said beam splitter into an electrical signal;
    an image rotating device positioned along the optical axis between the object and said light-sensitive electronic device;
    a rotating device for rotating said image rotating device at an angle of rotation with respect to the optical axis; and
    a processor for processing the electrical signal from said light-sensitive electronic device, thereby determining a physical characteristic of the object.

12. An optical device according to claim 11, wherein said image rotating device comprises a Dove prism.

13. An optical device according to claim 11, wherein said rotating device comprises a dc step motor.

14. An optical device according to claim 11, wherein said light-sensitive electronic device comprises a charge-coupled device.

15. An optical device according to claim 11, further comprising an aperture stop positioned between the object and said image rotating device.

16. An optical device, comprising:

an transparent optical medium having opaque markings, said optical medium directing a beam of light rays towards an object along an optical axis;

a one-dimensional light-sensitive electronic device positioned along the optical axis, said light-sensitive electronic device converting a two-dimensional image formed from the beam of light rays being reflected from the object and the image formed from the opaque markings on said optical medium into an electrical signal;

an image rotating device positioned along the optical axis between the object and said light-sensitive electronic device;

a rotating device for rotating said image rotating device at an angle of rotation with respect to the optical axis; and a processor for determining a physical and optical characteristic of the object based on a strength of the electrical signal from said light-sensitive electronic device.

17. An optical device according to claim 16, wherein said image rotating device comprises a Dove prism.

18. An optical device according to claim 16, wherein said rotating device comprises a d-c step motor.

19. An optical device according to claim 16, wherein said light-sensitive electronic device comprises a charge-coupled device.

20. An optical device according to claim 1, wherein the opaque markings on said beam splitter are located at angles of 0, 45, 90 and 135 degrees with respect to the optical axis.

21. An optical device according to claim 11, wherein the opaque markings on said beam splitter are located at angles of 0, 45, 90 and 135 degrees with respect to the optical axis.

22. An optical device according to claim 16, wherein the opaque markings on said beam splitter are located at angles of 0, 45, 90 and 135 degrees with respect to the optical axis.

* * * * *